United States Patent
Kapadia et al.

(10) Patent No.: US 11,998,288 B2
(45) Date of Patent: Jun. 4, 2024

(54) SURGICAL ROBOTIC SYSTEMS

(71) Applicant: Covidien LP, Mansfield, MA (US)

(72) Inventors: Jaimeen Kapadia, Cambridge, MA (US); Ranjan Mishra, Orange, CT (US)

(73) Assignee: COVIDIEN LP, Mansfield, MA (US)

( * ) Notice: Subject to any disclaimer, the term of this patent is extended or adjusted under 35 U.S.C. 154(b) by 611 days.

(21) Appl. No.: 17/273,441

(22) PCT Filed: Sep. 10, 2019

(86) PCT No.: PCT/US2019/050268
§ 371 (c)(1),
(2) Date: Mar. 4, 2021

(87) PCT Pub. No.: WO2020/060790
PCT Pub. Date: Mar. 26, 2020

(65) Prior Publication Data
US 2021/0338347 A1 Nov. 4, 2021

Related U.S. Application Data

(60) Provisional application No. 62/732,061, filed on Sep. 17, 2018.

(51) Int. Cl.
*A61B 34/30* (2016.01)
*A61B 17/00* (2006.01)
(Continued)

(52) U.S. Cl.
CPC .................. *A61B 34/30* (2016.02); *B25J 9/12* (2013.01); *A61B 2017/00017* (2013.01); *A61B 2017/00477* (2013.01); *A61B 34/37* (2016.02)

(58) Field of Classification Search
CPC ............... A61B 34/30; A61B 34/37; A61B 2017/00017; A61B 2017/00477; A61B 34/70; A61B 2034/302; B25J 9/12
(Continued)

(56) References Cited

U.S. PATENT DOCUMENTS 6,132,368 A 10/2000 Cooper
6,206,903 B1 3/2001 Ramans
(Continued)

FOREIGN PATENT DOCUMENTS

CN 103110456 A 5/2013
WO 2012068156 A2 5/2012
(Continued)

OTHER PUBLICATIONS

International Search Report dated Dec. 27, 2019, issued in corresponding international application No. PCT/US2019/050268, 9 pages.
(Continued)

*Primary Examiner* — Joseph M Dietrich
*Assistant Examiner* — Michael T. Holtzclaw
(74) *Attorney, Agent, or Firm* — Carter, DeLuca & Farrell, LLP

(57) ABSTRACT

An instrument drive unit for use in a robotic surgical system includes a carriage configured to be coupled to a robotic arm, a hub rotationally coupled to the carriage and configured to be non-rotatably coupled to an electromechanical surgical instrument, a plurality of electric motors disposed within the carriage, a plurality of drive shafts rotationally supported in the hub, and a plurality of drive gears. Each electric motor includes a stator and a rotor disposed within the stator. Each drive gear is fixed to a corresponding drive shaft and is configured for interfacing with a corresponding driven member of the electromechanical surgical instru-
(Continued)

ment. Each rotor is configured to rotate a corresponding drive gear in response to an activation of a respective electric motor to actuate a function of the electromechanical surgical instrument.

17 Claims, 5 Drawing Sheets

(51) Int. Cl.
    *B25J 9/12*     (2006.01)
    *A61B 34/37*     (2016.01)

(58) Field of Classification Search
    USPC .................................................................. 606/1
    See application file for complete search history.

(56) References Cited

U.S. PATENT DOCUMENTS

| | | |
|---|---|---|
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll et al. |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco et al. |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez et al. |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |

(56) References Cited

U.S. PATENT DOCUMENTS

| | | |
|---|---|---|
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart et al. |
| 8,989,903 B2 | 3/2015 | Weir et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,019,345 B2 | 4/2015 | O |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,931,170 B2 * | 4/2018 | Auld .................. A61B 34/30 |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 9,993,307 B2 | 6/2018 | Lohmeier |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |

(56) References Cited

U.S. PATENT DOCUMENTS

| | | |
|---|---|---|
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,265 B2 * | 6/2021 | Seow ................. A61B 34/70 |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 11,690,615 B2 * | 7/2023 | Parihar ................. A61B 17/282 |
| | | 227/176.1 |
| 2009/0160269 A1 * | 6/2009 | Bischof .................... H02K 3/47 |
| | | 606/1 |
| 2015/0094732 A1 | 4/2015 | Pacheco et al. |
| 2016/0066982 A1 | 3/2016 | Marczyk et al. |
| 2017/0065364 A1 | 3/2017 | Schuh et al. |
| 2017/0156803 A1 | 6/2017 | McGrogan et al. |
| 2018/0079090 A1 * | 3/2018 | Koenig .................... G01L 3/14 |
| 2018/0132955 A1 * | 5/2018 | Kapadia ................. A61B 34/30 |
| 2018/0133905 A1 * | 5/2018 | Smith .................. B25J 17/0241 |
| 2018/0163818 A1 | 6/2018 | Normandeau |
| 2018/0168748 A1 * | 6/2018 | Kapadia ................. A61B 17/29 |
| 2019/0261991 A1 * | 8/2019 | Beckman .......... A61B 17/32002 |
| 2019/0298464 A1 * | 10/2019 | Abbott .................... A61B 34/70 |
| 2021/0015572 A1 * | 1/2021 | Gomez .................. A61B 34/35 |
| 2021/0077213 A1 * | 3/2021 | Gomez .................. A61B 34/35 |
| 2021/0169593 A1 | 6/2021 | Kapadia |
| 2022/0168056 A1 * | 6/2022 | Seow .................... A61B 90/50 |

FOREIGN PATENT DOCUMENTS

| | | |
|---|---|---|
| WO | 2017151458 A1 | 9/2017 |
| WO | 2017205311 A1 | 11/2017 |
| WO | 2018041159 A1 | 3/2018 |

OTHER PUBLICATIONS

Supplementary European Search Report dated May 17, 2022, issued in corresponding EP Appln. No. 19862797, 10 pages.

Office Action issued in Chinese Patent Application No. 2019800588989 dated Oct. 28, 2023 (21 pages).

* cited by examiner

SURGICAL ROBOTIC SYSTEMS

BACKGROUND

Surgical robotic systems have been used in minimally invasive medical procedures. Some surgical robotic systems included a console supporting a surgical robotic arm and a surgical instrument having at least one end effector (e.g., forceps or a grasping tool) mounted to the robotic arm. The robotic arm provided mechanical power to the surgical instrument for its operation and movement.

Manually-operated surgical instruments often included a handle assembly for actuating the functions of the surgical instrument. However, when using a robotic surgical system, no handle assembly was typically present to actuate the functions of the end effector. Accordingly, to use each unique surgical instrument with a robotic surgical system, an instrument drive unit was used to interface with the selected surgical instrument to drive operations of the surgical instrument.

The instrument drive unit was typically coupled to the robotic arm via a slide. The slide allowed the instrument drive unit and the attached surgical instrument to move along an axis of the slide, providing a means for adjusting the axial position of the end effector of the surgical instrument.

SUMMARY

In accordance with an aspect of the present disclosure, an instrument drive unit for use in a robotic surgical system is provided and includes a carriage configured to be coupled to a robotic arm, a hub rotationally coupled to the carriage and configured to be non-rotatably coupled to an electromechanical surgical instrument, a plurality of electric motors disposed within the carriage, a plurality of drive shafts rotationally supported in the hub, and a plurality of drive gears. Each electric motor includes a stator and a rotor disposed within the stator. Each drive gear is fixed to a corresponding drive shaft and configured for interfacing with a corresponding driven member of the electromechanical surgical instrument. Each rotor is configured to rotate a corresponding drive gear in response to an activation of a respective electric motor to actuate a function of the electromechanical surgical instrument.

In aspects, each stator may be fixed relative to the carriage, and each rotor may be rotatable relative to and within a corresponding stator.

In some aspects, the electrical motors may be vertically stacked within the carriage.

In other aspects, the instrument drive unit may further include a drive motor including a stator fixed within the carriage, and a rotor disposed within the stator of the drive motor and non-rotatably coupled to the hub. The rotor of the drive motor may be configured to rotate the hub about a central longitudinal axis defined by the hub.

In further aspects, the instrument drive unit may further include a sleeve rotatably coupled to a distal end portion of the carriage and non-rotatably coupled to the hub. The sleeve may be configured to non-rotatably receive the electromechanical surgical instrument, such that a rotation of the hub results in a rotation of the electromechanical surgical instrument.

In aspects, the instrument drive unit may further include a plurality of ring gears. Each ring gear may be fixed to a corresponding rotor and operably coupled to a corresponding drive gear.

In some aspects, each ring gear may be concentrically disposed within a corresponding rotor, such that rotation of the rotor results in a rotation of the corresponding ring gear.

In other aspects, the ring gears may be vertically stacked within the hub.

In further aspects, a first electric motor, a first ring gear, and a first drive gear may be operably coupled to one another and aligned along a first horizontal plane, and a second electric motor, a second ring gear, and a second drive gear may be operably coupled to one another and aligned along a second horizontal plane, vertically displaced from the first horizontal plane.

In another aspect, the ring gears may be independently rotatable relative to one another.

In aspects, a first ring gear may have gear teeth on an inner periphery thereof. The gear teeth may interface with a corresponding drive gear, and an outer periphery of the first ring gear may be attached to an inner periphery of a corresponding rotor.

In some aspects, the drive shafts may be circumferentially spaced from one another.

In other aspects, the drive gears may be vertically offset from one another.

In other aspects, each drive shaft may have a distal end portion configured for interfacing with a corresponding driven member of the electromechanical surgical instrument.

In another aspect of the present disclosure, an instrument drive unit for use in a robotic surgical system is provided and includes a carriage configured to be coupled to a robotic arm, a plurality of electric motors supported in the carriage, and a plurality of drive shafts circumferentially spaced from one another. Each electric motor includes a stator and a rotor disposed within the stator. The drive shafts are configured for interfacing with a corresponding driven member of an electromechanical surgical instrument. Each drive shaft has a drive gear fixed thereabout, and each drive gear is disposed at a discrete vertical location relative to one another. Each rotor is configured to rotate a corresponding drive gear in response to an activation of a respective electric motor to actuate a function of the electromechanical surgical instrument.

In aspects, the instrument drive unit may further include a plurality of vertically stacked ring gears. Each ring gear may be fixed to a corresponding rotor and operably coupled to a corresponding drive gear, such that each rotor is configured to rotate a corresponding drive gear in response to an activation of a respective electric motor to actuate a function of the electromechanical surgical instrument.

In some aspects, the instrument drive unit may further include a hub rotationally coupled to the carriage, and a drive motor operably coupled to the hub. The hub may be configured to be non-rotatably coupled to the electromechanical surgical instrument. The drive shafts may be rotationally supported in the hub. The drive motor may be configured to rotate the hub about a central longitudinal axis defined by the hub.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Figure 1:
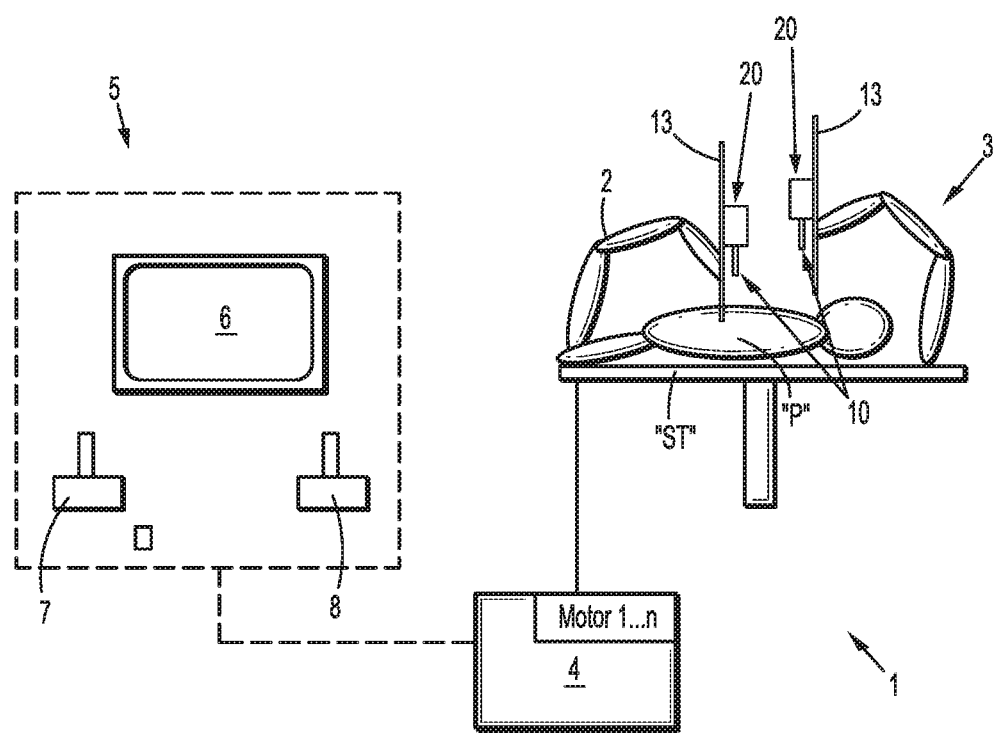
FIG. 1 is a schematic illustration of a surgical robotic system including an instrument drive unit coupled to a slide in accordance with the present disclosure.

Embodiments of the presently disclosed surgical robotic system and instrument drive units thereof are described in detail with reference to the drawings, in which like reference numerals designate identical or corresponding elements in each of the several views. As used herein, the term "distal" refers to that portion of the surgical robotic system or component thereof that is closest to the patient, while the term "proximal" refers to that portion of the surgical robotic system or component thereof further from the patient. As used herein, the term "vertical" refers to a direction defined along a longitudinal axis of a portion of the surgical robotic system, while the term "horizontal" refers to a direction defined along a transverse axis of a portion of the surgical robotic system.

As will be described in detail below, provided is an instrument drive unit of a surgical robotic system configured to allow for a bottom-loading of a surgical instrument. The instrument drive unit has a plurality of drive shafts each configured to be coupled to a corresponding driven member of the surgical instrument for carrying out a discrete function of the surgical instrument. The drive shafts of the instrument drive unit are operably coupled to a discrete electric motor of the instrument drive unit via a discrete transmission assembly. The configuration of the transmission assemblies allows for a reduction in the overall height of the instrument drive unit (e.g., the instrument drive unit is more compact). For example, gears of the transmission assemblies are vertically and horizontally offset from the gears of the other transmission assemblies. The instrument drive unit may also include a rotatable hub that rotationally supports the drive shafts. The hub is configured to be rotated via a separate drive motor to enable rotation of the attached surgical instrument about its longitudinal axis. Other features and benefits of the disclosed instrument drive units are further detailed below.

Referring initially to FIG. 1, a surgical system, such as, for example, a surgical robotic system 1, generally includes a plurality of surgical robotic arms 2, 3; an elongated slide 13 coupled to an end of each of the robotic arms 2, 3; an instrument drive unit 20 and an electromechanical instrument 10 removably attached to the slide 13 and configured to move along the slide 13; a control device 4; and an operating console 5 coupled with control device 4. The operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art.

Each of the robotic arms 2, 3 may be composed of a plurality of members, which are connected through joints. Robotic arms 2, 3 may be driven by electric drives (not shown) that are connected to control device 4. Control device 4 (e.g., a computer) is set up to activate the drives, in particular by means of a computer program, in such a way that robotic arms 2, 3, the attached instrument drive units 20, and thus electromechanical instrument 10 execute a desired movement according to a movement defined by means of manual input devices 7, 8. Control device 4 may also be set up in such a way that it regulates the movement of the instrument drive unit 20 along the slide 13, movement of the robotic arms 2, 3, and/or movement of the drives.

Surgical robotic system 1 is configured for use on a patient "P" lying on a surgical table "ST" to be treated in a minimally invasive manner by means of a surgical instrument, e.g., electromechanical instrument 10. Surgical robotic system 1 may also include more than two robotic arms 2, 3, the additional robotic arms likewise being connected to control device 4 and being telemanipulatable by means of operating console 5. A surgical instrument, for example, an electromechanical surgical instrument 10 (including an electromechanical end effector), may also be attached to the additional robotic arm.

Control device 4 may control a plurality of motors, e.g., motors (Motor 1 . . . n), with each motor configured to drive movement of robotic arms 2, 3 in a plurality of directions. Further, control device 4 may control a plurality of electric motors 22 (FIGS. 2-5) of the instrument drive unit 20 to drive various operations of the surgical instrument 10. The instrument drive unit 20 transfers power and actuation forces from its motors to driven members (not shown) of the electromechanical instrument 10 to ultimately drive movement of components of the end effector of the electromechanical instrument 10, for example, a movement of a knife blade (not shown) and/or a closing and opening of jaw members of the end effector.

For a detailed description of the construction and operation of a robotic surgical system, reference may be made to U.S. Pat. No. 8,828,023, entitled "Medical Workstation," the entire contents of which are incorporated by reference herein.

With reference to FIGS. 2-5, the instrument drive unit 20 will now be described in detail. The instrument drive unit 20 includes a carriage 26 (FIG. 4) and a coupling or sleeve 28 rotatably coupled to a distal end portion 26b of the carriage 26 for connecting a surgical instrument 10 (FIG. 1) to the instrument drive unit 20. The carriage 26 of the instrument drive unit 20 is configured to be slidably coupled to a linear track (not shown) defined longitudinally along the slide 13 (FIG. 1). A proximal end portion 26a of the carriage 26 houses a plurality of electric motors 22a, 22b, 22c, 22d, 22d, 22e (collectively referred herein as "22") for carrying out various functions of an attached surgical instrument 10.

The carriage 26 defines a longitudinally-extending channel 30 therethrough dimensioned for receipt of a hub 46 of the instrument drive unit 20. The distal end portion 26b has an annular ledge 32 (FIG. 4) that extends radially inward from an inner peripheral surface of the carriage 26. The annular ledge 32 is configured to support internal components of the instrument drive unit 20. In embodiments, the distal end portion 26b of the carriage 26 may have a slip ring 33 received therein for transferring electrical signals or power between fixed structures (e.g., the electric motors 22) and rotating structures (e.g., the electromechanical surgical instrument 10). The electrical signals transferred by the slip ring 33 may be feedback signals from the electromechanical surgical instrument 10 relating to the status and location of the surgical instrument 10 and/or the status and location of adjacent tissue structures. For example, the feedback may include the temperature of the surgical instrument 10, forces experienced by the surgical instrument 10, and/or the position of certain structures of the surgical instrument 10 relative to one another or relative to the adjacent tissue structures.

The coupling or sleeve 28 of the instrument drive unit 20 is rotatably coupled to the distal end portion 26b of the carriage 26. The sleeve 28 has a proximal end portion 28a received within the channel 30 of the carriage 26 and fixed to the hub 46, such that the sleeve 28 rotates with the hub 46. The sleeve 28 has a plurality of annular members 29 (FIG. 4) fixed therein having a respective drive shaft 66 extending therethrough. Rotation of the hub 46 causes the drive shafts 66 to rotate therewith, which, in turn, drives a rotation of the sleeve 28, as will be described. The sleeve 28 has a distal end portion 28b configured to non-rotationally fix the main body portion of the surgical instrument 10 therein. The sleeve 28 may have a pair of latch members 31a, 31b configured to releasably retain the main body portion of the electromechanical surgical instrument 10. Accordingly, when the surgical instrument 10 is coupled to the instrument drive unit 20, a rotation of the sleeve 28 results in a rotation of the attached surgical instrument 10.

The electric motors 22 of the instrument drive unit 20 are concealed within the carriage 26. The electric motors 22 are vertically stacked on one another and are independently actuatable via the control device 4 (FIG. 1). One of the electric motors, such as, for example, the fifth electric motor 22e, is configured to effectuate a rotation of the surgical instrument 10 when the surgical instrument 10 is coupled to the instrument drive unit 20, and the remaining electric motors 22a, 22b, 22c, 22d are configured to actuate functions of the surgical instrument 10, as will be described. The electric motors 22 are integrated AC motors. In embodiments, the electric motors 22 may be any suitable type of electric motor such as an AC brushless motor, a DC brushed motor, a DC brushless motor, a direct drive motor, a servo motor, a stepper motor, or the like. It is contemplated, and within the scope of the present disclosure, that electric motors 22 are in the form of hollow core motors, or the like. Other types of motors are also contemplated.

While the instrument drive unit 20 is illustrated as having five electric motors, it is contemplated that the instrument drive unit 20 may have more or less than five electric motors.

Figure 2:
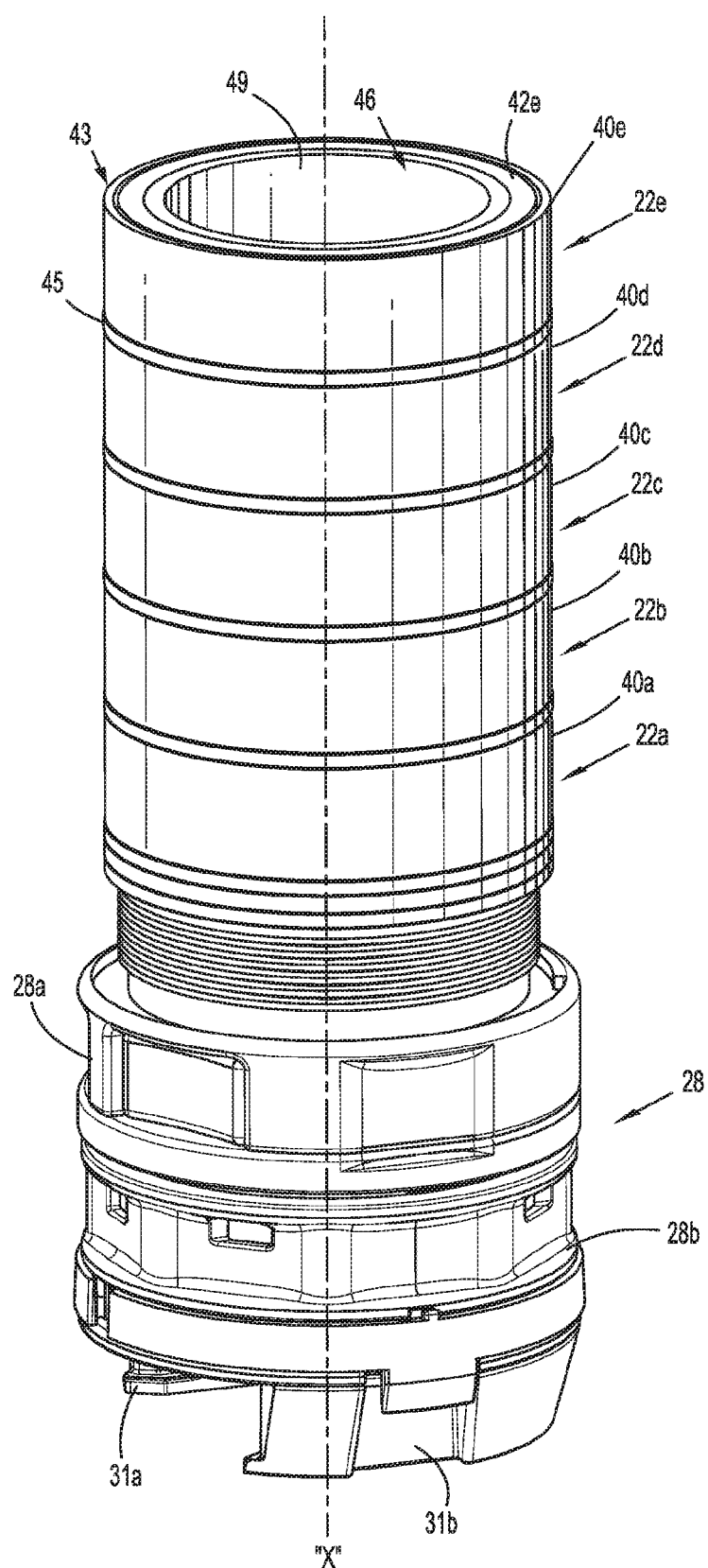
FIG. 2 is a perspective view of the instrument drive unit of the surgical robotic system of FIG. 1 with an outer carriage removed.

The electric motors 22 each have a stator 40a, 40b, 40c, 40d, 40e (collectively referred to herein as "40") fixed within the carriage, and a rotor 42a, 42b, 42c, 42d, 42e (collectively referred to herein as "42") rotationally disposed within a corresponding stator 40. Each of the stators 40 may be annularly shaped and stacked on top of one another to form a hollow cylinder 43, as best shown in FIG. 2. The stators 40 are electrically isolated from one another by having an insulative material 45 interposed between adjacent, vertically stacked stators 40. The stators 40 may be configured to receive an electric current from a power source (not explicitly shown) to produce a rotating magnetic field that drives a rotation of the rotors 42.

Each of the rotors 42 may be configured as a permanent magnetic, an electromagnet, or any other suitable conductor. The rotors 42 are vertically stacked within the hollow cylinder 43 formed by the stators 40 and are independently rotatable relative to one another about a central longitudinal axis "X" defined by the hollow cylinder 43. The rotors 42 may be rotationally supported on the insulative material 45. It is contemplated that a bearing 51 may be interposed between adjacent, vertically stacked rotors 42 to facilitate independent rotation of the rotors 42.

The hub 46 of the instrument drive unit 20 is supported in the hollow cylinder 43 formed by the stators 40. The hub 46 is configured to rotate relative to and within the hollow cylinder 43. The hub 46 has a pair of proximal and distal plates 58a, 58b disposed adjacent respective proximal and distal ends thereof. The plates 58a, 58b axially support the hub 46 in the carriage 26. The hub 46 has a plurality of support struts 47 extending vertically between the plates 58a, 58b, thereby connecting the plates 58a, 58b and providing integrity to the hub 46. The hub 46 further includes a ring member 49 extending proximally from the proximal plate 58a. The ring member 49 of the hub 46 has the rotor 42e of the fifth electric motor 22e disposed thereabout and fixed thereto. As such, a rotation of the rotor 42e of the fifth electric motor 22e drives a rotation of the hub 46 relative to the carriage 26 about the central longitudinal axis "X" defined by the hollow cylinder 43.

With continued reference to FIGS. 2-5, the instrument drive unit 20 further includes a plurality of transmission assemblies 60a, 60b, 60c, 60d (collectively referred to herein as "60") that function independently from one another to transfer torque from a corresponding electric motor 22 to a corresponding driven member of the attached surgical instrument 10. Each transmission assembly 60a, 60b, 60c, 60d may include a ring gear 62a, 62b, 62c, 62d (collectively referred to herein as "62"), a drive gear 64a, 64b, 64c, 64d (collectively referred to herein as "64"), and a drive shaft 66a, 66b, 66c, 66d (collectively referred to herein as "66") operably coupled to one another.

Components of the transmission assemblies 60 are vertically offset from one another along the central longitudinal axis "X" defined by the hollow cylinder 43, and certain components of each transmission assembly 60 are aligned along a horizontal plane. For example, the first ring gear 62a and the first drive gear 64a of the first transmission assembly 60a (e.g., the distal-most transmission assembly) are operably coupled to one another and substantially aligned along a first horizontal plane "P1," and the second ring gear 62b and the second drive gear 64b of the second transmission assembly 60b are operably coupled to one another and substantially aligned along a second horizontal plane "P2," which is vertically displaced (e.g., disposed distally) from the first horizontal plane "P1" along the longitudinal axis "X." The remaining transmission assemblies 60c and 60d are also disposed in a discrete horizontal plane. While only four transmission assemblies are shown, it is contemplated that the instrument drive unit 20 may have more or less than four transmission assemblies.

The ring gears 62 of the transmission assemblies 60 are vertically stacked within the hollow cylinder 43. In particular, the ring gears 62 are coaxial along the central longitudinal axis "X" defined by the hollow cylinder 43. The ring gears 62 are disposed about the support struts 47 of the hub 46 and are interposed between the proximal and distal plates 58a, 58b of the hub 46.

Figure 5:
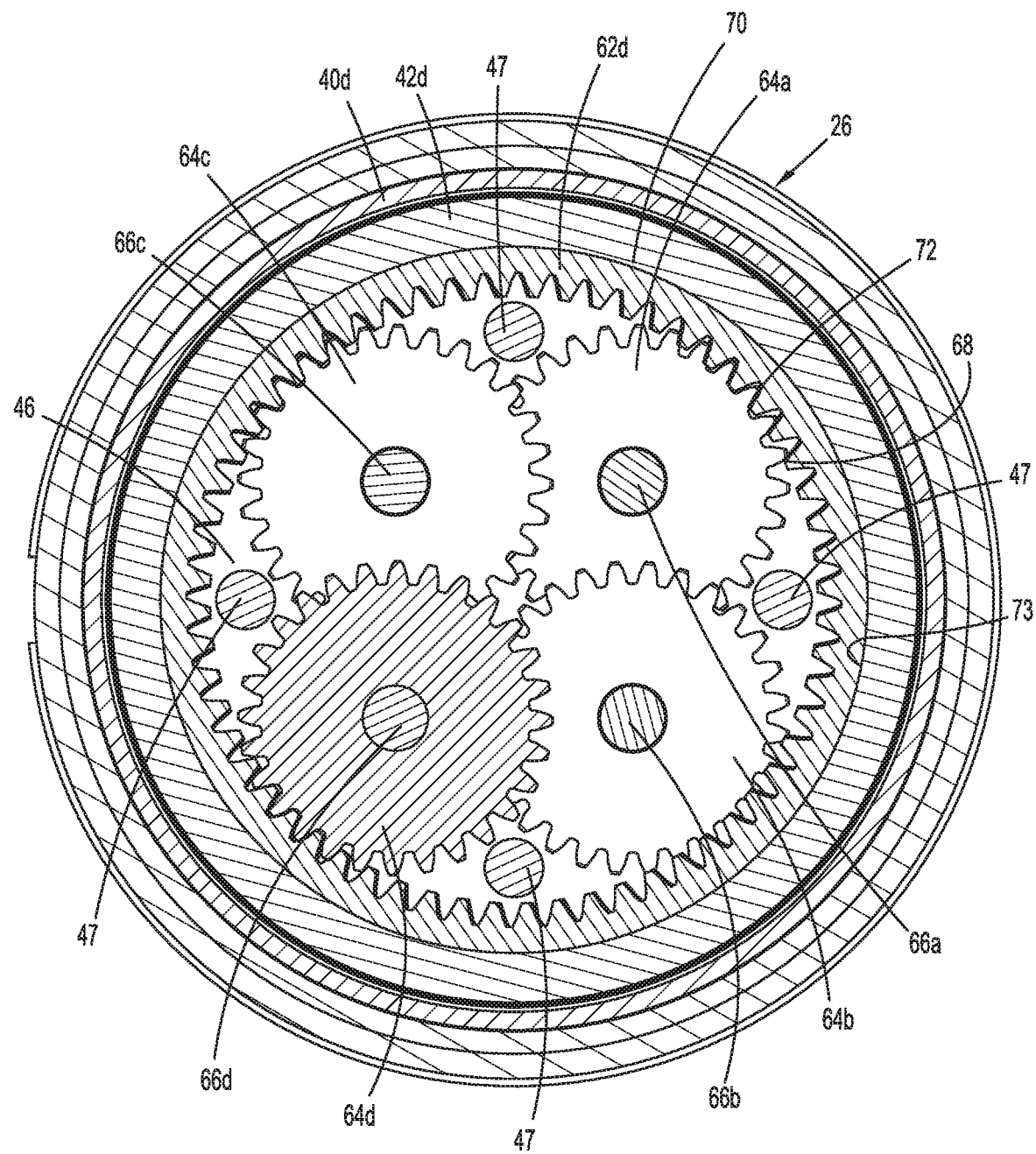
FIG. 5 is a side cross-sectional view of the instrument drive unit of FIG. 2.

As best shown in FIG. 5, each of the ring gears 62 has an outer periphery 70 adhered to an inner periphery 73 of a respective rotor 42, such that each ring gear 62 and rotor 42 pair (e.g., ring gear 62d and rotor 42d) rotate together relative to the corresponding stator 40. Each ring gear 62 has gear teeth 68 extending from an inner periphery 72 thereof. The gear teeth 68 on the inner periphery 72 of each of the ring gears 62 interfaces with a corresponding drive gear 64, as will be described. In embodiments, each of the rings gears 62 may be constructed as a rotor 42 rather than being integrally connected with a rotor 42.

Figure 3:
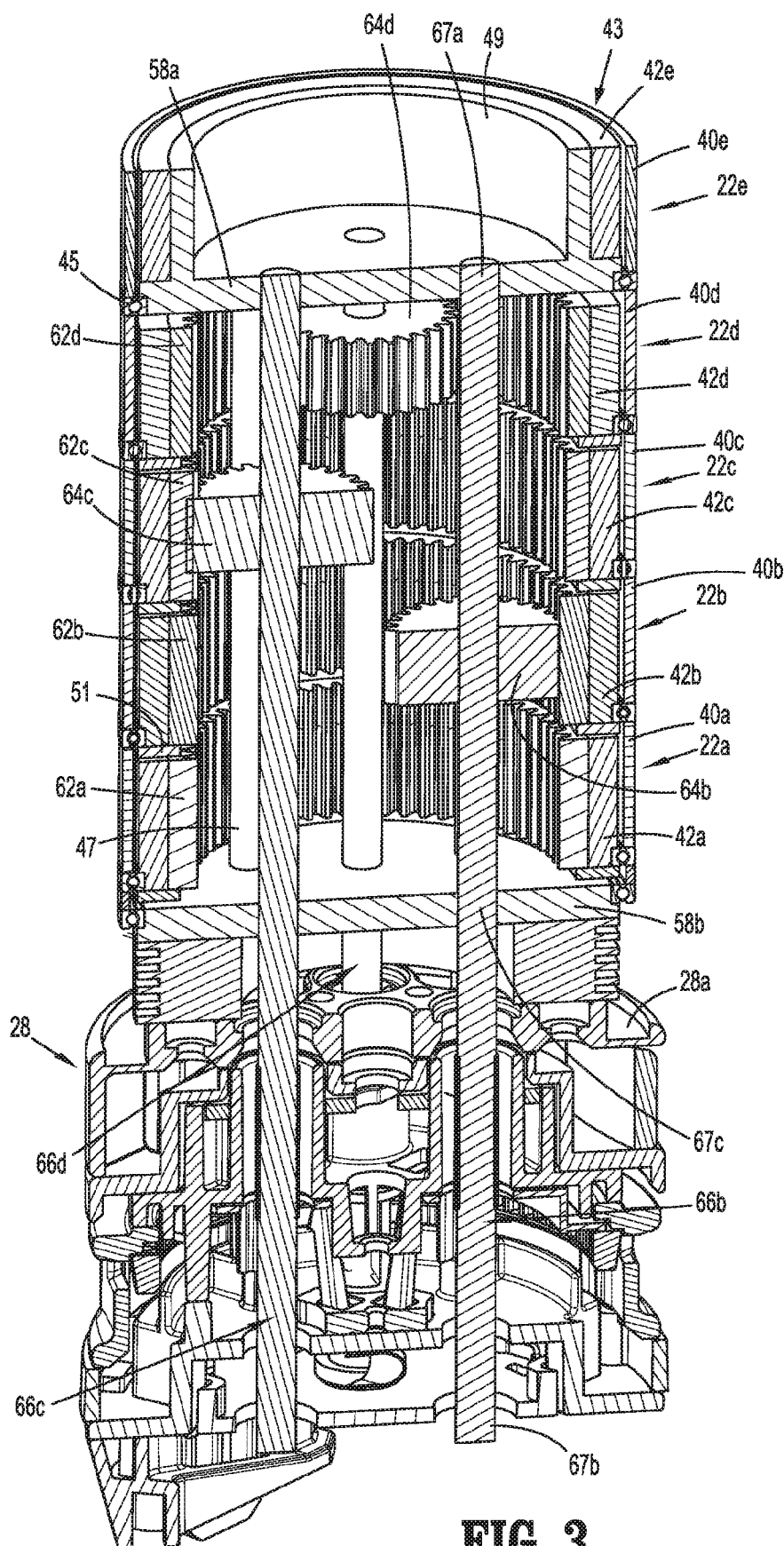
FIG. 3 is a longitudinal cross-sectional view of the instrument drive unit of FIG. 2 with the outer carriage removed.
Figure 4:
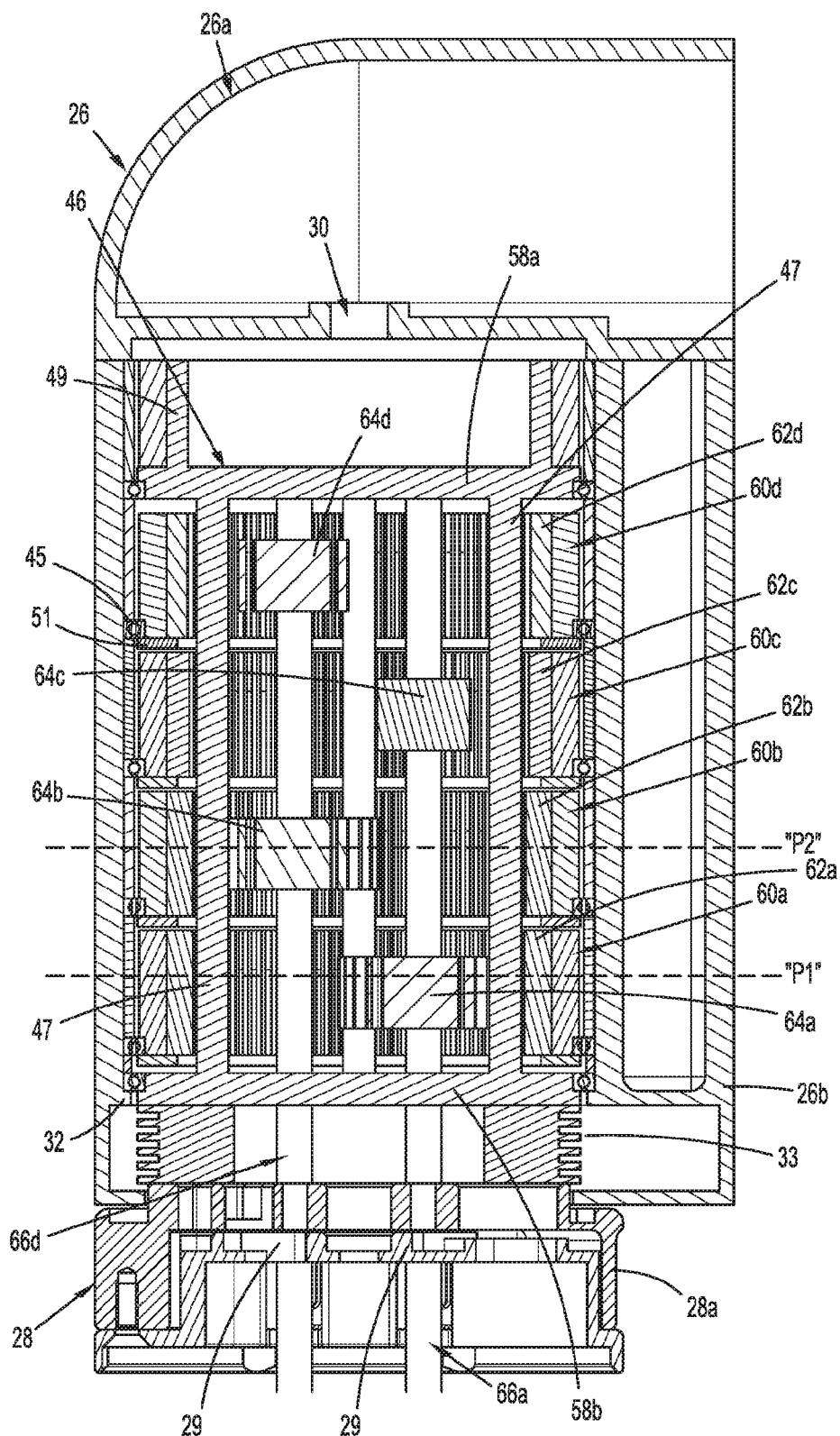
FIG. 4 is another longitudinal cross-sectional view of the instrument drive unit of FIG. 2 with the outer carriage shown.

With reference to FIGS. 3-5, the drive shafts 66a, 66b, 66c, 66d of the transmission assemblies 60a, 60b, 60c, 60d extend longitudinally through the hub 46 and distally therefrom. In particular, each of the drive shafts 66 has a proximal end portion 67a rotatably coupled to the proximal plate 58a of the hub 46, an intermediate portion 67c extending between the proximal and distal plates 58a, 58b of the hub 46, and a distal end portion 67b extending distally from the distal plate 58b of the hub 46. The drive shafts 66 are circumferentially spaced from one another about the central longitudinal axis "X" of the hollow cylinder 43. The drive shafts 66 are free to rotate about their respective longitudinal axes in relation to the hub 46.

The distal end portion 67b of each of the drive shafts 66 is configured to operably couple to a driven member (not explicitly shown) of the surgical instrument 10. For example, the distal end portion 67b of each of the drive shafts 66 may have a coupler (e.g., a gear) for coupling with a corresponding coupler of a driven member of the surgical instrument 10. Accordingly, upon bottom-loading of the electromechanical instrument 10 into the instrument drive unit 20, the distal end portions 67b of the drive shafts 66 of the instrument drive unit 20 operably couple to the gears/couplers in a distal end of the main body portion (not shown) of the electromechanical instrument 10, such that a rotation of each drive shaft 66 rotates a correspondingly coupled driven member of the surgical instrument 10 to effectuate a discrete function of the surgical instrument (e.g., opening/closing of the end effector, articulation of the end effector, etc.)

The drive shafts 66 each have a drive gear 64 such as, for example, a spur gear, rotationally fixed thereabout. Each of the drive gears 64 are positioned at a discrete vertical location on their respective drive shaft 66, such that the drive gears 64 are vertically offset a selected distance from one another. Since the drive gears 64, in addition to being vertically offset, are also circumferentially spaced from one another, the drive gears 64 are offset from one another in all three dimensions. As mentioned above, the drive gears 64 each interface or intermesh with the gear teeth 68 on the inner periphery 72 of a corresponding ring gear 62 and receive torque therefrom originating from the respective rotor 42.

In operation, the electromechanical instrument 10 is coupled to the instrument drive unit 20 by passing the main body portion of the electromechanical instrument 10 through the sleeve 28 of the instrument drive unit 20 in a proximal direction. The latch members 31a, 31b of the sleeve 28 may engage opposing lateral sides of the main body portion of the surgical instrument 10 (FIG. 1) to selectively retain the surgical instrument 10 within the sleeve 28. With the main body portion of the electromechanical instrument 10 attached to the sleeve 28 of the instrument drive unit 28, the distal end portion 67b of each of the drive shafts 66 interfaces with corresponding gears/couplers (not shown) in the proximal end of the main body portion of the electromechanical instrument 10.

With the electromechanical instrument 10 coupled to the instrument drive unit 20, to actuate a particular function of the surgical instrument 10, such as, for example, an opening or closing of an end effector of the surgical instrument 10, one of the electric motors 22 of the instrument drive unit 20, such as the first electric motor 22a, is activated via the control device 4 (FIG. 1). An activation of the first electric motor 22a includes supplying an electric current to the stator 40a thereof, which drives a rotation of the rotor 42a thereof. It is contemplated that the control device 4 or a processor (not shown) of the electric motor 22a generates a rotating magnetic field about the stator 40a to drive the rotation of the rotor 42a. Rotation of the rotor 42a actuates the first transmission assembly 60a to transfer torque from the rotor 42a to a first driven member of the electromechanical instrument 10.

An actuation of the first transmission assembly 60a includes a rotation of the first ring gear 62a of the first transmission assembly 60a with the rotor 42a, which, in turn, rotates the first drive gear 64a of the first transmission assembly 60a. Since the first drive gear 64a is rotationally fixed about the first drive shaft 66a, and the distal end portion 67b of the first drive shaft 66a is operably coupled to the proximal end of the first driven member of the surgical instrument 10 (FIG. 1), a rotation of the first drive gear 64a causes the first drive shaft 66a to rotate, thereby rotating the first driven member of the electromechanical instrument 10 to actuate an associated function of the surgical instrument 10.

It is contemplated that the fifth electric motor 22e may be configured to resist rotation of the rotor 42e thereof during actuation of any of the transmission assemblies 60a, 60b, 60c, 60d so that actuation of one of the transmission assemblies 60a, 60b, 60c, 60d does not inadvertently result in a rotation of the hub 46.

To rotate the electromechanical instrument 10 about its longitudinal axis, the fifth electric motor 22e of the instrument drive unit 20 is activated by the control device 4 (FIG. 1). An activation of the fifth electric motor 22e includes supplying an electric current to the stator 40e thereof, which drives a rotation of the rotor 42e thereof. Rotation of the rotor 42e rotates the hub 46 about the central longitudinal axis "X" since the rotor 42e is fixed to the ring member 49 of the hub 46. Due to the drive shafts 66 extending through the distal plate 58b of the hub 46 and the annular members 29 (FIG. 4) of the sleeve 28, the sleeve 28 rotates with the hub 46. Given that the electromechanical instrument 10 is non-rotationally supported in the sleeve 28, the electromechanical instrument 10 rotates with the sleeve 28 relative to the carriage 26 to change a rotational orientation of the electromechanical instrument 10.

The electric motors 22a, 22b, 22c, 22d may be configured to synchronously rotate the rotors 40a, 40b, 40c, 40d, and in turn the drive gears 64a, 64b, 64c, 64d, with the rotation of the hub 46. This would prevent rotation of the drive shafts 66a, 66b, 66c, 66d about their respective longitudinal axes during rotation of the hub 46, which may otherwise occur if the drive gears 64a, 64b, 64c, 64d were held stationary during rotation of the hub 46. Conversely, the fifth motor 22e may be actuated during an actuation of one of the electric motors 22a, 22b, 22c, 22d to so that any torque transferred through one of the drive shafts 64 will not result in rotation of the hub 46.

As can be appreciated, the instrument drive unit 20 described above improves usability of the surgical robotic system 1, reduces a foot-print of the overall system 1, improves safety architecture, reduces the time required to remove surgical instruments in case of an emergency, and simplifies the electronics used in the instrument drive unit 20.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. An instrument drive unit for use in a robotic surgical system, the instrument drive unit comprising:
   a carriage configured to be coupled to a robotic arm;
   a hub rotationally coupled to the carriage and configured to be non-rotatably coupled to an electromechanical surgical instrument;
   a plurality of electric motors disposed within the carriage, each electric motor of the plurality of electric motors including a stator and a rotor disposed within the stator, wherein each stator is fixed relative to the carriage, and each rotor is rotatable relative to and within a corresponding stator, and wherein the plurality of electrical motors are vertically stacked within the carriage;
   a plurality of drive shafts rotationally supported in the hub; and
   a plurality of drive gears, each drive gear of the plurality of drive gears fixed to a corresponding drive shaft of the plurality of drive shafts and configured for interfacing with a corresponding driven member of the electromechanical surgical instrument, wherein each rotor is configured to rotate a corresponding drive gear of the plurality of drive gears in response to an activation of a respective electric motor of the plurality of electric motors to actuate a function of the electromechanical surgical instrument.

2. The instrument drive unit according to claim 1, further comprising a sleeve rotatably coupled to a distal end portion of the carriage and non-rotatably coupled to the hub, wherein the sleeve is configured to non-rotatably receive the electromechanical surgical instrument, such that a rotation of the hub results in a rotation of the electromechanical surgical instrument.

3. The instrument drive unit according to claim 1, further comprising a plurality of ring gears, each ring gear of the plurality of ring gears fixed to a corresponding rotor and operably coupled to a corresponding drive gear of the plurality of drive gears.

4. The instrument drive unit according to claim 3, wherein each ring gear of the plurality of ring gears is concentrically disposed within the corresponding rotor, such that rotation of the rotor results in a rotation of the corresponding ring gear of the plurality of ring gears.

5. The instrument drive unit according to claim 3, wherein the plurality of ring gears are vertically stacked within the hub.

6. The instrument drive unit according to claim 3, wherein a first electric motor of the plurality of electric motors, a first ring gear of the plurality of ring gears, and a first drive gear of the plurality of drive gears are operably coupled to one another and aligned along a first horizontal plane, and wherein a second electric motor of the plurality of electric motors, a second ring gear of the plurality of ring gears, and a second drive gear of the plurality of drive gears are operably coupled to one another and aligned along a second horizontal plane, vertically displaced from the first horizontal plane.

7. The instrument drive unit according to claim 3, wherein at least a first ring gear of the plurality of ring gears has gear teeth on an inner periphery thereof, wherein the gear teeth on the inner periphery of the first ring gear interface with the corresponding drive gear of the plurality of drive gears, and an outer periphery of the first ring gear is attached to an inner periphery of the corresponding rotor.

8. The instrument drive unit according to claim 1, wherein the plurality of drive shafts are circumferentially spaced from one another.

9. The instrument drive unit according to claim 1, wherein the plurality of drive gears are vertically offset from one another.

10. The instrument drive unit according to claim 1, wherein each drive shaft of the plurality of drive shafts has a distal end portion configured for interfacing with a corresponding driven member of the electromechanical surgical instrument.

11. An instrument drive unit for use in a robotic surgical system, the instrument drive unit comprising:
    a carriage configured to be coupled to a robotic arm;
    a hub rotationally coupled to the carriage and configured to be non-rotatably coupled to an electromechanical surgical instrument;
    a plurality of electric motors disposed within the carriage, each electric motor of the plurality of electric motors including a stator and a rotor disposed within the stator;
    a plurality of drive shafts rotationally supported in the hub;
    a plurality of drive gears, each drive gear of the plurality of drive gears fixed to a corresponding drive shaft of the plurality of drive shafts and configured for interfacing with a corresponding driven member of the electromechanical surgical instrument, wherein each rotor is configured to rotate a corresponding drive gear of the plurality of drive gears in response to an activation of a respective electric motor of the plurality of electric motors to actuate a function of the electromechanical surgical instrument; and
    a drive motor including:
      a stator fixed within the carriage; and
      a rotor disposed within the stator of the drive motor and non-rotatably coupled to the hub, wherein the rotor of the drive motor is configured to rotate the hub about a central longitudinal axis defined by the hub.

12. An instrument drive unit for use in a robotic surgical system, the instrument drive unit comprising:
    a carriage configured to be coupled to a robotic arm;
    a hub rotationally coupled to the carriage and configured to be non-rotatably coupled to an electromechanical surgical instrument;
    a plurality of electric motors disposed within the carriage, each electric motor of the plurality of electric motors including a stator and a rotor disposed within the stator;
    a plurality of drive shafts rotationally supported in the hub;
    a plurality of drive gears, each drive gear of the plurality of drive gears fixed to a corresponding drive shaft of the plurality of drive shafts and configured for interfacing with a corresponding driven member of the electromechanical surgical instrument, wherein each rotor is configured to rotate a corresponding drive gear of the plurality of drive gears in response to an activation of a respective electric motor of the plurality of electric motors to actuate a function of the electromechanical surgical instrument; and
    a plurality of ring gears, each ring gear of the plurality of ring gears fixed to a corresponding rotor and operably coupled to a corresponding drive gear of the plurality of drive gears, wherein the plurality of ring gears are independently rotatable relative to one another.

13. An instrument drive unit for use in a robotic surgical system, the instrument drive unit comprising:
- a carriage configured to be coupled to a robotic arm;
- a plurality of electric motors supported in the carriage, each electric motor of the plurality of electric motors including a stator and a rotor disposed within the stator;
- a plurality of drive shafts circumferentially spaced from one another and configured for interfacing with a corresponding driven member of an electromechanical surgical instrument, each drive shaft of the plurality of drive shafts having a drive gear fixed thereabout, each drive gear being disposed at a discrete vertical location relative to one another, wherein each rotor is configured to rotate a corresponding drive gear in response to an activation of a respective electric motor of the plurality of electric motors to actuate a function of the electromechanical surgical instrument;
- a hub rotationally coupled to the carriage and configured to be non-rotatably coupled to the electromechanical surgical instrument, the plurality of drive shafts being rotationally supported in the hub; and
- a drive motor operably coupled to the hub and configured to rotate the hub about a central longitudinal axis defined by the hub.

14. The instrument drive unit according to claim 13, further comprising a plurality of vertically stacked ring gears, each ring gear of the plurality of ring gears fixed to a corresponding rotor and operably coupled to the corresponding drive gear, such that each rotor is configured to rotate the corresponding drive gear in response to an activation of a respective electric motor of the plurality of electric motors to actuate a function of the electromechanical surgical instrument.

15. The instrument drive unit according to claim 14, wherein a first electric motor of the plurality of electric motors, a first ring gear of the plurality of ring gears, and a first drive gear attached to a first drive shaft of the plurality of drive shafts are operably coupled to one another and aligned along a first horizontal plane, and wherein a second electric motor of the plurality of electric motors, a second ring gear of the plurality of ring gears, and a second drive gear attached to a second drive shaft of the plurality of drive shafts are operably coupled to one another and aligned along a second horizontal plane, vertically displaced from the first horizontal plane.

16. The instrument drive unit according to claim 14, wherein each ring gear of the plurality of ring gears is concentrically disposed within the corresponding rotor, such that rotation of the rotor results in a rotation of a corresponding ring gear of the plurality of ring gears.

17. The instrument drive unit according to claim 13, wherein the drive motor includes:
- a stator fixed within the carriage; and
- a rotor disposed within the stator of the drive motor and non-rotatably coupled to the hub, wherein the rotor of the drive motor is configured to rotate the hub about the central longitudinal axis defined by the hub.

* * * * *